US008802079B2

(12) United States Patent
Knap et al.

(10) Patent No.: US 8,802,079 B2
(45) Date of Patent: *Aug. 12, 2014

(54) **BILE RESISTANT *BACILLUS* COMPOSITION**

(75) Inventors: Inge Knap, Broenshoej (DK); Ane Knarreborg, Lynge (DK); Thomas Dyrmann Leser, Frederiksberg (DK); Lund Bente, Frederiksberg (DK); Mette Dines Cantor, Birkeroed (DK); Patrick Derkx, Tikoeb (DK)

(73) Assignee: Chr. Hansen A/S, Hoersholm (DK)

( * ) Notice: Subject to any disclaimer, the term of this patent is extended or adjusted under 35 U.S.C. 154(b) by 38 days.

This patent is subject to a terminal disclaimer.

(21) Appl. No.: 13/139,894

(22) PCT Filed: Dec. 16, 2009

(86) PCT No.: PCT/EP2009/067317
§ 371 (c)(1),
(2), (4) Date: Jul. 11, 2011

(87) PCT Pub. No.: WO2010/070005
PCT Pub. Date: Jun. 24, 2010

(65) Prior Publication Data
US 2011/0262584 A1  Oct. 27, 2011

(30) Foreign Application Priority Data
Dec. 19, 2008 (EP) .................................... 08389501

(51) Int. Cl.
*A01N 63/00* (2006.01)
*C12N 1/20* (2006.01)
*C12P 1/04* (2006.01)

(52) U.S. Cl.
USPC .................... 424/93.462; 435/170; 435/252.5

(58) Field of Classification Search
None
See application file for complete search history.

(56) References Cited

U.S. PATENT DOCUMENTS

| | | | |
|---|---|---|---|
| 4,844,934 A | 7/1989 | Lueddecke et al. | |
| 5,571,547 A | 11/1996 | Serpelloni et al. | |
| 6,255,098 B1* | 7/2001 | Oh et al. | 435/252.5 |
| 6,500,473 B1 | 12/2002 | Koehler et al. | |
| 6,984,406 B2* | 1/2006 | Cho et al. | 426/53 |
| 8,334,123 B2* | 12/2012 | Knap et al. | 435/170 |
| 2002/0018770 A1 | 2/2002 | Maruta et al. | |
| 2002/0026886 A1 | 3/2002 | Isager et al. | |
| 2003/0124104 A1* | 7/2003 | Farmer | 424/93.46 |
| 2005/0152851 A1 | 7/2005 | Kaminski | |
| 2008/0113076 A1 | 5/2008 | Klingenberg | |
| 2009/0010857 A1 | 1/2009 | Waterfield | |

FOREIGN PATENT DOCUMENTS

| | | |
|---|---|---|
| EP | 0 239 086 B1 | 6/1992 |
| EP | 0 287 699 B1 | 7/1993 |
| EP | 1 300 394 B1 | 2/2004 |
| EP | 1 066 761 B1 | 9/2004 |
| EP | 1 875 814 A1 | 1/2008 |
| EP | 1 964 479 A1 | 9/2008 |
| EP | 1 967 081 A1 | 9/2008 |
| EP | 1 967 196 A1 | 9/2008 |
| EP | 2 011 858 A1 | 1/2009 |
| EP | 1 471 151 B1 | 11/2009 |
| JP | 11-43430 | 2/1999 |
| WO | WO 94/11492 | 5/1994 |
| WO | WO 97/33976 | 9/1997 |
| WO | WO 99/03449 | 1/1999 |
| WO | WO-02/08182 A1 | 1/2002 |
| WO | WO 03/039260 A2 | 5/2003 |
| WO | WO 2004/015084 | 2/2004 |
| WO | WO 2004/080200 A1 | 9/2004 |
| WO | WO-2006/032339 A1 | 3/2006 |
| WO | WO-2007/003543 A1 | 1/2007 |
| WO | WO-2007/009601 A1 | 1/2007 |
| WO | WO-2007/090614 A1 | 8/2007 |
| WO | WO 2008/087173 A1 | 7/2008 |
| WO | WO 2009/007192 A1 | 1/2009 |
| WO | WO 2009/007273 A2 | 1/2009 |

OTHER PUBLICATIONS

ATCC Catalogue. ATCC Bacteria and Bacteriophages. 19th edition, 1996, pp. 60 and 61.*
http://www.chr-hansen.com/gallipro.html XP002461911, Oct. 12, 2007.
B. Hyronimus et al., "Acid and bile tolerance of spore-forming lactic acid bacteria", International Journal of Food Microbiology, 61 (2000) 193-197.
G. Cenci et al., "Tolerance to challenges miming gastrointestinal transit by spores and vegetative cells of *Bacillus clausii*", Journal of Applied Microbiology, 101 (2006) 1208-1215.
M.E. Sanders et al., "Sporeformers as Human Probiotics: *Bacillus, Sporolactobacillus*, and *Brevibacillus*", Institute of Food Technologies, vol. 2, 2003—Comprehensive Reviews in Food Science and Food Safety, pp. 101-110.
Le H. Duc et al., "Characterization of *Bacillus* Probiotics Available for Human Use" Applied and Environmental Microbiology, Apr. 2004, vol. 70, No. 4, pp. 2161-2171.
Huynh A. Hong et al., "The use of bacterial spore formers as probiotics", FEMS Microbiology Reviews 29, (2005), 813-835.
http://www.stocarstvo.com/ishrana/probiotics_in_broilers.htm
Carvalho & Hansen: Prospects for probiotics in broilers, Feed International, vol. 26 Nov. 2005, pp. 1-3.
L.M. Wijnands et al., "Spores from mesophilic *Bacillus cereus* strains germinate better and grow faster in simulated gastro-intestinal conditions than spores from psychorotrophic strains", International Journal of Food Microbiology 112, (2006), pp. 120-128.

(Continued)

*Primary Examiner* — Vera Afremova
(74) *Attorney, Agent, or Firm* — Foley & Lardner LLP

(57) ABSTRACT

A bacillus composition characterized by fast germination and outgrowth in bile salts (simulated gut environment) and by producing a compound of interest. The bacillus composition may be used as supplement in animal feed where it has a probiotic (health promoting) effect and increases the digestion and availability of nutrients from animal feeds.

7 Claims, 2 Drawing Sheets

(56) References Cited

OTHER PUBLICATIONS

Xiaohua Guo et al., "Screening of *Bacillus* strains as potential probiotics and subsequence confirmation of the in vivo effectiveness of *Bacillus subtilis* MA139 in pigs", Antonie van Leeuwenhock (2006) 90: 139-146.

Database WPI, Week, Apr. 4, 2002, XP002461912: KR 20020225395.

Carvalho N. Hansen S: "Prospects for probiotics in broilers" Feed International, [Online] vol. 26, No. 10, Nov. 2005, http://www.stocarstvo.com/ishrana/probiotics_in_broilers.html [retrieved on Dec. 10, 2007].

International Search Report PCT/EP2009/067273 dated Mar. 11, 2010.

Gabriella Casula et al., "*Bacillus* Probiotics: Spore Germination in the Gastrointestinal Tract", Applied and Environmental Microbiology, May 2002, vol. 68, No. 5, pp. 2344-2352.

Harutoshi Tsuda et al., "High bile- and low pH-resistant lactic acid bacteria isolated from traditional fermented dairy products in Inner Mongolia, China", Milk Science vol. 55, No. 3, 2007, pp. 129-134. Database WPI Week 200646, XP002465172, Jun. 22, 2006.

S. Drusch et al., "Microencapsulation properties of two different types of n-octenylsuccinate-derivatised starch", Eur Food Res Technol (2006) 222, pp. 155-164.

Thomas E. Furia, "Colour Additives in Food", CRC Handbook of Food Additives, Jan. 1, 1981, CRC Press, pp. 612-613.

Anonymous, "Speciality starches provide superior emulsification and encapsulation", Jan. 21, 2004, pp. 1-2 retrieved from the internet, XP002569407.

E.B. Jackson, "Sugar Confectionery Manufacture", Second Edition, Blackie Academic and Professional, 1995.

J. Smith et al., "Food Additives Data Book", 2003, Blackwell Science Ltd. XP002524085, pp. 304-306.

* cited by examiner

Figure 1: *B.subtilis* strains
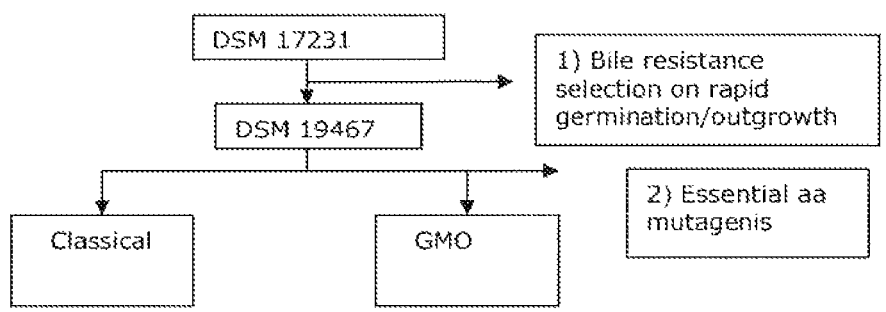

Figure 2A:
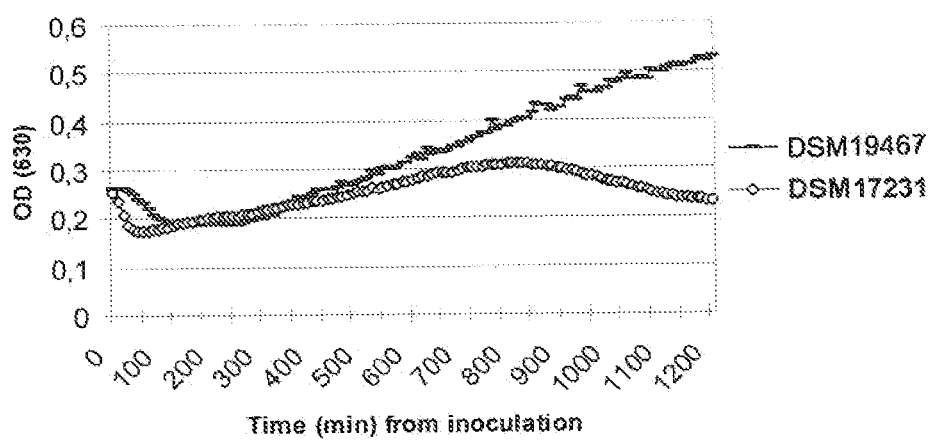

Figure 2A (4mM) and 2B (6mM). Time (min) from $10^6$ spores/ml until OD $0.4_{630}$ is reached

BILE RESISTANT *BACILLUS* COMPOSITION

FIELD OF THE INVENTION

The present invention relates to a bacillus composition characterized by fast germination and outgrowth in bile salts (simulated gut environment) and by producing a compound of interest. The bacillus composition may be used as supplement in animal feed where it has a probiotic (health and growth promoting) effect and increases the digestion and availability of nutrients from animal feeds.

BACKGROUND ART

Probiotic bacteria such as *Bacillus subtilis* and *Bacillus licheniformis* are used in the animal feed industry as supplement to the diet. Their usage is related to the ability of bacillus to replace or reduce the use of antibiotics, which are used as growth promoters in the animal feed industry.

Christian Hansen A/S, Denmark commercializes an example of such a probiotic growth-promoting product under the trade name GalliPro® (deposited as DSM 17231). GalliPro® is a *Bacillus subtilis* spore cell composition.

Besides the suggested mode of actions (e.g. immune modulation, gut flora modifier) probiotic bacillus are able to produce many beneficial components, such as enzymes, which are excreted in the gastro intestinal tract (GIT) when used as animal feed supplement. Enzymes such as phytase are excreted and improve the digestion and better uptake of animal feed (higher digestibility). The diet (feed) is mostly composed of plant origin such as grains, corn, soybean, soy oil and amino acids. Overall these effects contribute to the production of cost effective animal products.

Probiotic bacilli are also able to produce other beneficial components such as essential amino acids.

Bacillus spores can pass the acidic gastric barrier and germinate and outgrow within the gastrointestinal (GIT) of the animals. This has great advantages, since when invested they can excrete numerous types of beneficial components, e.g. bacteriocins and also excrete useful essential amino acids. Moreover, the bacillus spores are thermostabile during a feed pelletizing process and are thereby an excellent delivery system to get both bacteriocins and e.g. essential amino acids into the GIT.

In the survival and proliferation process of bacillus in GIT, the role of bile is important. Bile is produced in the liver and stored in the gallbladder. Bile contains water, lecithin, bilirubin and biliverdin and bile salts.

It is known from the literature that bile has some negative influences on the survival and germination and outgrowth of bacillus spore cells to vegetative cells in the GIT of animals. Therefore research is ongoing to find probiotic bile resistant Bacillus strains.

The article (Antonie Van Leeuwenhoek. 2006 August; 90(2): 139-46. Epub 2006 July 4) describes isolation of a number of Bacillus samples/cell directly from the intestine of chickens. The isolated bacillus cells were tested for probiotic activity. The six bacilli with highest probiotic activity were testes for bile salt resistance and it was found that a specific highly probiotic bacillus has a relatively high level of bile salt resistance.

In this article there is no special focus on any time periods for the testing of bile resistance. In the experimental part the bacillus spore cells are simply tested for resistance after 5 days of presence in bile salt (see paragraph "Simulated small intestinal fluid tolerance test" on page 141).

US2003/0124104A describes that probiotic conventional bacillus endospores are sensitive to low concentration of bile salts, i.e. spore germination and/or rehydration is inhibited by the presence of even low concentrations of bile salts. This is contrary to other bacteria such as enteric pathogens, such as *E. coli* or *S. aureus* (see section [0014] to [0015]). In view of this it is suggested to screen/select for bacillus spores that are resistant to the inhibitory activity of bile salts, and as a result, germinate into vegetative cells, which then colonize the colon (see [0019]).

The working examples are all in presence and no real experimental data of actually screened specific Bacillus cell are provided in the description.

Further the bile salt screening conditions are relatively generically described. In particular there are no indications of any time periods for the selections of bile resistance. Said in other words, based on the only broad/generic teaching of this document one may select Bacillus cells that only can outgrow (germinate) slowly, i.e. are capable of germinating from spores to vegetative cells after e.g. 20 hours in presence of relevant amount of bile salt.

In this document there is no description or suggestion to select for bacillus cells that can outgrow (germinate) rapidly, i.e. capable of germinating and outgrowing from spores to vegetative cells reaching a defined growth point within a certain time interval in presence of a relevant amount of bile salt.

In summary, the prior art references relating to selection/screening of bile resistant bacillus cells are not focusing on rapid outgrowth/germination from spore cells to vegetative bacillus cells.

International PCT application with application number PCT/EP2008/057296 was filed Nov. 6, 2008. Applicant is Chr. Hansen A/S and it was NOT PUBLISHED at the filing date of this present application.

PCT/EP2008/057296 describes novel bacillus spores characterized by having an improved/rapid speed of germination and outgrowth from spore to vegetative cell in presence of a bile salt medium.

The bacillus spores as described herein have the same improved/rapid speed of germination and outgrowth from spore to vegetative cell as described in PCT/EP2008/057296.

PCT/EP2008/057296 only describes bacillus vegetative cells that are producing phytase in an increased amount as compared to the reference bacillus cell DSM 19467.

As can be seen below, in first aspect and claim 1 herein is disclaimed such high producing phytase bacillus cells of PCT/EP2008/057296.

When there below is referred to prior art this shall be understood as prior art made available to the public (e.g. published articles/patents) at the filing date of this present application.

SUMMARY OF THE INVENTION

The problem to be solved by the present invention is to provide a bacillus composition which can excrete high amounts of beneficial compounds in the gastro intestinal tract (GIT) of an animal.

The solution is based on that the present inventors have developed a novel selection method for the identification of new improved bacillus compositions.

A novel important step of the herein described new selection method is to specifically screen/select for bacillus spore cells with improved/rapid speed of germination and outgrowth from spores to vegetative cells in the presence of bile salts.

As described above, the prior art has described methods for selecting bacillus cells capable of growing in presence of bile salts, but the prior art screening/selection methods do NOT focus on the speed of germination and outgrowth in the presence of bile salt. Accordingly, the prior art selected bile resistant bacillus cells do not germinate and grow fast enough to comply with the speed of germination and outgrowth criteria as described herein. For instance, bacillus cells isolated directly from the intestine of e.g. chickens (as e.g. described in the Antonie Van Leeuwenhoek article discussed above) in the gut environment are not selected (under natural pressure) to germinate and outgrow rapidly in the intestine.

As shown in working examples herein this is also true for the commercial available Bacillus composition GalliPro®, which simply germinates and outgrows too slowly and does not reach the defined growth point within the first 20 hours in presence of physiological levels of bile salts to comply with the speed of germination and outgrowth criteria as described herein. GalliPro® is a *Bacillus subtilis* composition that is commercially successful.

The herein described novel DSM 19467 was selected by using GalliPro® as a starting strain and a selective pressure method and a subsequent isolation for rapid germination and outgrowth from spores to vegetative cells in presence of bile salt as described herein.

See e.g. table 1 for further details (GalliPro® may herein also be termed DSM 17231).

In FIG. 1 herein this is illustrated schematically.

In summary, it is believed that no prior art describes an isolated Bacillus composition, which comprises from $10^5$ to $10^{12}$ CFU/g bacillus cells, wherein the cells of the bacillus composition complies with the rapid germination and outgrowth in the presence of bile salt criteria as described herein.

Without being limited to theory, the present inventors have identified that rapid germination and outgrowth is a very important aspect of the invention as bacillus spores, which are resistant to bile but do not germinate and outgrow fast enough, will be excreted before any positive characteristics, such as essential amino acid production, can be made in significant amounts by the vegetative bacillus cells.

Bacillus spores germinating too slowly will simply pass through the gastro intestinal tract (GIT) before the bacteria can produce any significant amount of e.g. essential amino acids.

After a number of detailed tests and analysis, the inventors therefore chose to work with a time range up to 20 hours and select the fastest germinating and outgrowing spores within this time period in presence of high physiological concentrations of bile salts. Without being limited to theory and based on the herein disclosed detailed experimental work, the present inventors have identified that it is important to have a rapid germination and outgrowth within the first 18 and 19 hours in the presence of 4 and 6 mM bile salt, respectively.

The present inventors then identified that once bacillus cells, with rapid germination and outgrowth in bile salt medium, have been selected these cells are highly useful as starting cells for mutagenesis to obtain new cells with improved essential amino acid production.

As illustrated schematically in FIG. 1 and example 4, the rapid outgrowing bile resistant selected strain, DSM 19467, was used as starting strain for classical mutation and the high essential amino acid producing strain were selected. As can be seen in example 4, some of the selected strains produce at least 5 times more of the essential amino acid leucine than DSM 19467 and GalliPro®.

As discussed above, in our earlier application PCT/EP2008/057296 DSM 19467 was use to make new high phytase producing strains—see for instance example 4 of PCT/EP2008/057296.

The description of PCT/EP2008/057296 is incorporated herein by reference.

Accordingly, one may see DSM 19467 as a very useful kind of e.g. "intermediate" to make new bacillus cells with improved properties such as e.g. higher phytase or essential amino acid production or any other relevant compound of interest.

Further, it is evident to the skilled person that once the inventors herein have disclosed the ESSENTIAL test assay for testing rapid germination and outgrowth of example 1 plus the identified strain DSM 19467 it will be routine work for the skilled person to select other new bacillus cells complying with the criteria of the first aspect herein—i.e. other alternative bacillus cells with similar characteristic to DSM 19467.

Accordingly, a first aspect of the invention relates to a bacillus composition, which comprises from $10^5$ to $10^{12}$ CFU/g bacillus spore cells, wherein the bacillus composition is characterized by:

(i): the bacillus spores have a rapid germination and outgrowth from spore to vegetative cell in presence of a bile salt medium comprising 4 and 6 mM bile salts, defined by that the bacillus spores reach a vegetative cell growth point of 0.4 $OD_{630}$ within less than 18 and 19 hours, respectively, wherein the vegetative cell growth point is the point in the growth curve where the OD value starts to increase (due to growth of the vegetative cells) in a continuous way and reaches an $OD_{630}$ of 0.4;

(I): wherein the bile salt medium is the standard known non-selective Veal Infusion Broth (VIB) medium of example 1 herein supplemented with a bile salt mixture comprising the conjugated bile salts taurodeoxycholate and glycodeoxycholate and the deconjugated bile salt deoxycholate in the proportions 60% of the taurodeoxycholate, 30% of the glycodeoxycholate and 10% of deoxycholate; and wherein the OD assay analysis is performed by the following steps:

(a): filling a well in a microtiter plate with 0.150 ml bile salt medium having $10^8$ bacillus spores per ml medium (i.e. this is time zero); and (b): incubating the plate at 37° C. under atmospheric conditions and measuring the $OD_{630}$ values, using a spectrophotometer and with agitation before each reading, to get a representative growth curve over time;

and (ii) the bacillus vegetative cells are producing a relevant compound of interest;

and with the proviso that the bacillus vegetative cells are NOT cells as described in claim 1 of PCT/EP2008/057296, wherein the bacillus vegetative cells of item (ii) are producing phytase in an amount of at least 1.25 times more than the reference bacillus cell DSM 19467, wherein the produced phytase amount is measured by the standard phytase assay of example 2 of PCT/EP2008/057296 after 4 hours growth at 37° C. in the standard known non-selective Heart Infusion Broth (HIB) medium of example 2 of PCT/EP2008/057296;

and wherein the phytase assay analysis is performed by the following steps:

(a): making a overnight culture of bacillus vegetative cells in a enriched culture medium; and (b): transferring a 1% inoculum from the overnight culture to HIB medium (i.e. this is time zero) and incubation at 37° C. until phytase activity measurement.

The term "a relevant compound of interest" of point (ii) should be understood broadly. As discussed above, bacillus cells with spores that comply with criteria (i) of first aspect can in principle e.g. be used as a starting strain to screen for bacillus vegetative cells that may e.g. have higher/improved production of any compound of interest—such as e.g. an enzyme of interest.

As discussed above, the reference bacillus cell DSM 19467 is selected for rapid germination and outgrowth in presence of bile salt by using GalliPro® as starting strain. DSM 19467 is not selected for improved production of a compound of interest (e.g. an essential amino acid). Without being limited to theory, it is believed that the herein relevant production of the vast majority of commercial relevant compounds of interest (e.g. phytase or an essential amino acid) of DSM 19467 corresponds to GalliPro® production of the same compound.

In relation to point (i) the vegetative cell growth point for GalliPro® is at least 20 hours after incubation in 4 and 6 mM bile salt and for the novel DSM 19467 strain, as described herein, it is after 14 and 15 hours in 4 and 6 mM bile salts, respectively (see FIG. 2 and working example 3 herein).

It is here relevant to note that the present inventors also tested the commercial available product CALSPORIN® (Calpis Co., Ltd., Japan) to determine the vegetative cell growth point under the conditions of point (i) of first aspect. As for GalliPro® the commercial product CALSPORIN® is a *Bacillus subtilis* composition used as a probiotic feed additive. The vegetative cell growth point under the conditions of point (i) of first aspect for CALSPORIN® was more than 20 hours at 4 and 6 mM bile salts, respectively. This is considerably more than the 18 and 19 hours required under point (i) and this illustrates that commercially available products have hitherto not been selected for rapid germination and outgrowth. As discussed above, "natural" bacillus cells have not been under any selective pressure to get rapid germination and outgrowth. Without being limited to theory, it is therefore believed that "natural" bacillus cells are not complying with the conditions of point (i) of first aspect.

Both the bile resistance [of point (i)] and essential amino acid assay [of point (ii)] are based on known, commercially available standard elements (such as e.g. standard media, bile salts; standard OD measurements and standard tests).

The reference bacillus cell is deposited as DSM 19467 and is therefore publicly available.

The *Bacillus subtilis* cell GalliPro® is deposited as DSM 17231 (named "GalliPro®") and is therefore publicly available.

Accordingly, based on the detailed assay description herein (see e.g. example 1 herein for bile resistance assay and example 2 herein for essential amino acid assay) the skilled person is routinely able to repeat these assays to objectively determine whether a specific bacillus cell of interest complies with the bile resistance [of point (i)] and essential amino acid [of point (ii)] levels of the first aspect of the invention.

The novel bacillus composition as described herein may be used as a probiotic supplement to animal feed. The dose and administration may be done according to the art as for instance as done for prior art GalliPro® bacillus compositions.

Accordingly, a second aspect of the invention relates to a method for feeding an animal comprising administering the bacillus composition of first aspect and herein described related embodiments to an animal in conjunction with other animal feed ingredients.

A third aspect of the invention relates to a method for screening and isolating a novel bacillus cell comprising the following steps:
(a): selecting and isolating from a pool of individual bacillus spore cells of a new bacillus spore cell that is capable of germinating and outgrowing so rapidly that it reaches a vegetative cell growth point within less than 18 and 19 hours under the conditions of point (i) of first aspect;
(b): making a vegetative bacillus cell from the isolated spore cell of step (a) and mutating the novel selected and isolated cell to get a pool of new individual bacillus vegetative cells;
(c): selecting and isolating from the pool of new individual bacillus vegetative cells of step (b) a new bacillus vegetative cell that is capable of producing a relevant compound of interest; and
(d): analyzing the vegetative bacillus cell of step (c) to confirm that it has maintained the rapid germination and outgrowth of step (a) and isolating the selected bacillus cell.

It is evident to the skilled person that once the inventors herein have disclosed the relevant test assays (in particular the assay for testing rapid germination and outgrowth of example 1) plus the reference strain DSM 19467 it will be routine work for the skilled person to select other new bacillus cells complying with the criteria of the first aspect herein.

As discussed herein, by using the novel screening/selection method as described herein the inventors have selected and isolated a number of new improved bacillus cells.

Embodiment of the present invention is described below, by way of examples only.

Definitions

All definitions of herein relevant terms are in accordance of what would be understood by the skilled person in relation to the herein relevant technical context.

The term "bacillus cell" relates herein to both a bacillus spore cell and a bacillus vegetative cell.

The term "bacillus spore" in relation to bacillus spore cell relates herein to a spore that according to the art may be characterized as a dormant, tough, non-reproductive structure produced by bacillus bacteria. The primary function of spores is generally to ensure the survival of a bacterium through periods of environmental stress. They are therefore resistant to ultraviolet and gamma radiation, desiccation, lysozyme, temperature, starvation, and chemical disinfectants. Spores are commonly found in soil and water, where they may survive for long periods of time. The spore coat is impermeable to many toxic molecules and may also contain enzymes that are involved in germination. The core has normal cell structures, such as DNA and ribosomes, but is metabolically inactive. When a bacterium detects that environmental conditions are becoming unfavorable it may start the process of sporulation, which takes about eight hours.

The term "bacillus vegetative cell" relates to functional vegetative bacillus cells, which can divide to produce more vegetative cells.

The term "germination and outgrowth" relates to that bacillus spores germinate and outgrow to bacillus vegetative cells. As know to the skilled person reactivation of the spore occurs when conditions are favorable and involves germination and outgrowth. Germination involves the dormant spore starting metabolic activity and thus breaking hibernation. It is commonly characterized by rupture or absorption of the spore coat, swelling of the spore, an increase in metabolic activity, and loss of resistance to environmental stress. Outgrowth follows germination and involves the core of the spore manufacturing new chemical components and exiting the old spore coat to develop into a functional vegetative bacterial cell, which can divide to produce more cells.

Growth curves (OD versus time) of bacillus cells show distinct growth phases. As the spores are transferred to a nutrient rich medium the germination is initiated followed by a temporary decrease in OD (phase I), which is due to the release of dipicolinic acid and consequently hydration of the spore coat. In the second phase (phase II=outgrowth phase) there is a period with a relative little change in OD, until the spores are developed into a functional vegetative bacterial cells, which can divide to produce more cells and thereby give a continuous increase in OD value. The point when one starts to get the continuous increase in OD values reaching an OD of 0.4 is herein termed "vegetative cell growth point".

The term "optical density" is defined as a measure of optical absorbance using a spectrophotometer. Optical density (OD) is the absorbance of an optical element for a given wavelength λ per unit distance. If OD is e.g. measured at wavelength 630 nm it may be referred to as $OD_{630}$.

DRAWINGS

FIG. 1: In this figure the steps to get to the herein novel improved strains are illustrated. The working examples herein were started from DSM 17231 (GalliPro®), which was classically mutated and screened/selected for rapid germination and outgrowth in presence of bile salt to get the novel selected strain DSM 19467. DSM 19467 was used as starting strain for classical mutation and high essential amino acid producing strains were selected.

Figure 2B:
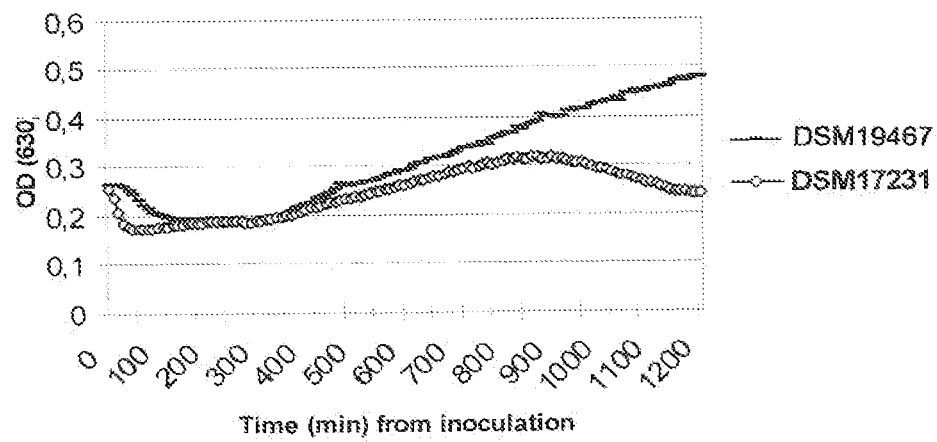

FIGS. 2a and 2b: These figures show clearly the improved rapid germination and outgrowth of DSM 19467 bacillus spores of the present invention as compared to DSM 17231 in presence of 4 and 6 mM bile salt as described herein.

DETAILED DESCRIPTION OF THE INVENTION

A Relevant Compound of Interest:

As discussed above, the term "a relevant compound of interest" of point (ii) should be understood broadly. As discussed above, bacillus cells with spores that comply with criteria (i) of first aspect—such as e.g. DSM 19467—can in principle e.g. be used as a starting strain to screen for bacillus vegetative cells that may e.g. have higher/improved production of any compound of interest—such as e.g. an enzyme of interest.

Suitable examples of a compound of interest may be enzymes such as e.g. mannanase. A compound of interest could also be an essential amino acid such as leucine.

In a preferred embodiment of point (ii) of the first aspect the bacillus vegetative cells are producing the compound of interest in an amount that is higher than the reference bacillus cell DSM 19467, wherein both the vegetative cell and reference bacillus cell DSM 19467 are grown under identical conditions.

In example 4 herein on can see an example of this embodiment—in example 4 herein is described vegetative cells with at least 5 times higher production of the essential amino acid leucine as compared to DSM 19467.

Further, as discussed above—in example 4 of PCT/EP2008/057296 is described similarly for phytase—i.e. vegetative cells with higher production of phytase as compared to DSM 19467.

Bacillus Composition:

The term "bacillus composition" shall be understood according to the art. It is herein understood as a bacillus composition comprising a number of bacillus spore cells with a characteristic of interest.

The bacillus composition may comprise different types of bacillus cells (e.g. *B. subtilis* and *Bacillus licheniformis*). In essence the composition shall simply comprise the amount of bacillus spore cells given in the first aspect herein, wherein the bacillus cells comply with the criteria given in the first aspect.

As known to the skilled person, herein commercially relevant bacillus spore cell compositions are generally made by fermentation. The obtained spore cells are generally concentrated, dried, mixed with a carrier and packed into a suitable container.

The relevant e.g. $10^5$ to $10^{12}$ CFU/g bacillus cells of the composition may be present in a commercially relevant form known to the skilled person.

Accordingly, in an embodiment $10^5$ to $10^{12}$ CFU/g bacillus spore cells of the composition are present as dried (e.g. spray dried) cells or as frozen spore cells.

In a preferred embodiment the bacillus composition comprises from $10^6$ to 1012 CFU/g bacillus spore cells, more preferably from $10^7$ to $10^{12}$ CFU/g bacillus spore cells.

The term "CFU/g" relates to the gram weight of the composition as such, including suitable relevant additives present in the composition. It does not include the weight of a suitable container used to package the bacillus composition.

An embodiment relates to that the bacillus composition is packaged into a suitable container.

As known to the skilled person a commercially relevant bacterial composition generally also comprises other relevant additives such as e.g. one carrier/ingredient of the group belonging to whey, whey permeate, calcium carbonate/limestone and anti caking agents such as aluminum silicates and kieselgur (diatomaceous earth).

Beside the herein relevant bacillus cells the composition may also comprise other relevant microorganisms of interest such as e.g. lactic acid bacteria of interest.

Bacillus Cell

The bacillus cell may be any relevant bacillus cell of interest.

In a preferred embodiment the bacillus cell is at least one bacillus cell selected from a bacillus species selected from the group consisting of:

*Bacillus subtilis, Bacillus uniflagellatus, Bacillus laterop-sorus, Bacillus laterosporus* BOD, *Bacillus megaterium, Bacillus polymyxa, Bacillus licheniformis, Bacillus pumilis,* and *Bacillus sterothermophilus, Bacillus coagulans, Bacillus thermophilus, Bacillus mycoides, Bacillus cereus,* and *Bacillus circulans.*

In a more preferred embodiment the bacillus cell is a *B. subtilis* cell or a *Bacillus licheniformis* cell.

The most preferred is wherein the bacillus cell is a *B. subtilis* cell.

Assay to Select for Rapid Germination and Outgrowth in the Presence of Bile Salt As discussed above the bile resistance assay of point (i) of first aspect is based on known commercially available standard elements (such as e.g. standard media, bile salts; standard OD measurements).

Accordingly, based on the detailed assay description herein (see e.g. example 1 herein) the skilled person is routinely able to repeat this assay to objectively determine whether a specific bacillus spore cell of interest complies with the rapid germination and outgrowth from spore to vegetative cell criteria as described in point (i).

In point (i) it is explained that vegetative cell growth point is the point in a growth curve starting with $10^8$ spores/ml corresponding to OD of around 0.2-0.3 until the time where the OD value has increased (due to growth of the vegetative cells) in a continuous way and has reached OD 0.4. This is in accordance with how a skilled person would understand such a vegetative cell growth point and based on a growth curve the skilled person may routinely determine this, within a limited variability of around ±30 minutes, as explained herein.

Working example 1 herein provides a detailed description of a bile resistance assay suitable to select for rapid germination and outgrowth in the presence of bile salt.

The detailed conditions of this example 1 is herein a preferred assay to determine if a *bacillus* spore cell of interest complies with the criteria of point (i) of first aspect.

The term "bile salt" relates to the salt of bile acids. Bile acids are steroid acids found predominantly in the bile of mammals. They are produced in the liver by the oxidation of cholesterol, and are stored in gallbladder and secreted into the intestine in the form of salts. They act as surfactants, emulsifying lipids and assisting with their absorption and digestion. The bile salts used in example 1 were prepared mimicking the physiological concentrations and compositions of porcine bile salts. As known to the skilled person porcine bile salts compositions may herein be considered as relatively "harsh" conditions as compared to avian bile salt compositions.

The term "bile salt medium" relates to medium comprising relevant bacillus growth ingredients such as relevant nutrients and bile salt.

Vegetative Cell Growth Point—in Bile Salt Assay—Point (i) of First Aspect

As said above, in relation to point (i) of first aspect the bacillus spore cells, as described herein, have a germination and outgrowth from spore to vegetative cell that is so rapid that they reach a vegetative cell growth point of 0.4 OD within less than 18 and 19 hours at 4 and 6 mM bile salts, respectively.

As said above, the novel DSM 19467 strain reaches the vegetative cell growth point after 14 and 15 hours incubation in 4 and 6 mM bile salt, respectively.

Accordingly, in a preferred embodiment the bacillus spores reach the vegetative cell growth point after 17 and 18 hours incubation in 4 and 6 mM bile salt under the conditions of point (i) of first aspect, more preferably the bacillus spores reach the vegetative cell growth point after 15 and 16 hours incubation in 4 and 6 mM bile salt under the conditions of point (i) of first aspect.

As explained above and shown schematically in FIG. 1 the herein described novel DSM 19467 strain was selected by using the commercially available GalliPro® as a starting strain for mutagenesis and selection for rapid outgrowth in presence of bile salt as described herein.

GalliPro® is a composition comprising *Bacillus subtilis* cells and the *Bacillus subtilis* is deposited as DSM 17231. Accordingly, GalliPro® may herein be seen as a reference strain.

As said above, the vegetative cell growth starting point for GalliPro® is after 20 hours incubation in 4 and 6 mM bile salts under the conditions of point (i) of first aspect. Accordingly, in an embodiment the bacillus spores reach the vegetative cell growth point at least 3 hours earlier than the reference *Bacillus subtilis* spores cells deposited as DSM 17231 ("GalliPro®") under the conditions of point (i) of first aspect, more preferably the bacillus spores reach the vegetative cell growth point at least 4 hours earlier than the reference *Bacillus subtilis* spores cells deposited as DSM 17231 ("GalliPro®") under the conditions of point (i) of first aspect, and most preferably the bacillus spores reach the vegetative cell growth starting point at least 5 hours earlier than the reference *Bacillus subtilis* spores cells deposited as DSM 17231 ("GalliPro®") under the conditions of point (i) of first aspect.

Essential Amino Acids

As known to the skilled person an essential amino acid may be an essential amino acid selected from the group consisting of: phenylalanine, valine, threonine, tryptophan, isoleucine, methionine, leucine, lysine, cysteine, tyrosine, histidine and arginine.

In a preferred embodiment the essential amino acid is at least one essential amino acid selected from the group consisting of: phenylalanine, valine, threonine, tryptophan, isoleucine, methionine, leucine, and lysine.

In more preferred embodiment the essential amino acid is at least one essential amino acid selected from the group consisting of: valine, isoleucine and leucine.

A herein very relevant essential amino is leucine.

As understood by the skilled person, the bacillus vegetative cells may produce higher amount of more than one essential amino acid, such as e.g. higher amount of two or three or more different essential amino acids.

Amino Acid Assay

As discussed above the amino acid assay of point (ii) of first aspect is based on standard known commercially available elements (such as e.g. standard media, standard test).

Accordingly, based on the detailed assay description herein (see e.g. example 2 herein) the skilled person is routinely able to repeat this assay to objectively determine whether a specific bacillus vegetative cell of interest complies with the produced essential amino acid amount as described in point (ii).

Working example 2 herein provides a detailed description of a essential amino acid assay.

The detailed conditions of this example 2 are herein a preferred essential amino acid assay to determine if a bacillus vegetative cell of interest complies with the criteria of point (ii) of first aspect.

Produced Amount of Essential Amino Acid—Point (ii) of First Aspect

In relation to point (ii) of first aspect, the Bacillus vegetative cells are preferably producing at least one essential amino acid in an amount of at least 2 times more than the reference Bacillus cell DSM 19467 under the conditions of point (ii) of first aspect.

In a more preferred embodiment in relation to point (ii) of first aspect, the Bacillus vegetative cells are preferably producing at least one essential amino acid in an amount of at least 4 times more than the reference Bacillus cell DSM 19467 under the conditions of point (ii) of first aspect.

A Method for Feeding/Administering Bacillus Spores to an Animal

As said above a second aspect of the invention relates to a method for feeding an animal comprising administering the bacillus composition of first aspect and herein described related embodiments to an animal in conjunction with other animal feed ingredients.

The animal may be any animal of interest. Preferably, the animal is an animal selected from the group consisting of poultry, ruminants, calves, pigs, rabbits, horses, fish and pets.

When administering GalliPro® according to the art it is normally done in a dose from around $10^4$-$10^8$ CFU/g feed, commonly $10^5$-$10^6$ CFU/g feed or in doses equivalent to normal feed intake/kg live weight animal.

Alternatively the bacillus spores may be administered to the animal in one of the following ways:
(1): put it into drinking water for animals;
(2): sprayed onto animals; or
(3): application via paste, gel or bolus.

A Method for Screening and Isolating a Novel Bacillus Cell

As said above, the third aspect relates to a method for screening and isolating a novel bacillus cell.

In the method of the third aspect is selected for a bacillus cell capable of fulfilling the conditions of point (i) and (ii) of the first aspect.

As understood by the skilled person, the specific herein detailed described bile resistance and essential amino acid amount assay (see e.g. example 1 herein for bile resistance assay and example 2 herein for essential amino acid assay) parameters may be changed to make a alternative screening method that still obtains the main goals as described herein, i.e. a bacillus cell that is capable of fulfilling the conditions of point (i) and (ii) of the first aspect.

In a preferred embodiment, bile resistance assay of example 1 is used in step (a) of the screening method of third aspect and the essential amino acid assay of example 2 is used in step (c) of the screening method of third aspect.

In step (d) of the screening method of third aspect a vegetative bacillus cell is isolated. This vegetative bacillus cell may be used to make bacillus spores from.

Accordingly, in an embodiment the screening method of third aspect is followed by a extra step (e), wherein the isolated bacillus vegetative cell of step (d) is fermented to make from $10^5$ to $10^{12}$ bacillus vegetative cells and these $10^5$ to $10^{12}$ bacillus vegetative cells are used to make $10^5$ to $10^{12}$ bacillus spore cells, which are isolated to give a Bacillus composition, which comprises from $10^5$ to $10^{12}$ CFU/g bacillus spore cells.

The end result of step (e) is a novel Bacillus composition, which comprises from $10^5$ to $10^{12}$ CFU/g bacillus spore cells, and wherein the bacillus cells are capable of fulfilling the conditions of point (i) and (ii) of the first aspect.

Accordingly, a separate aspect of the invention relates to a Bacillus composition, which comprises from $10^5$ to $10^{12}$ CFU/g bacillus spore cells, and wherein the bacillus cells are capable of fulfilling the conditions of point (i) and (ii) of the first aspect obtainable by the screening method of third aspect followed by extra step (f) described above.

In step (b) of the screening method of third aspect is made mutations of the earlier selected bile resistant bacillus cell to select for high essential amino acid producing cells in step (c). As understood by the skilled person this may e.g. by classical mutation (e.g. by chemical treatments or UV) of specific exchange of genes to make a so-called Genetic Modified Organism (GMO).

Deposited Strains

A sample of the novel *Bacillus subtilis* strain has been deposited at DSMZ (Deutsche Sammlung von Mikroorganismen and Zellkulturen GmbH, Maschroder Weg 1b, D-38124 Braunschweig) under the accession number DSM 19467 with a deposit date of Jun. 27, 2007. The deposit has been made under the conditions of the Budapest Treaty on the International Recognition of the Deposit of Microorganisms for the Purposes of Patent Procedure.

EXAMPLES

Example 1

Bile Resistance Assay

Medium:

The medium was a standard non-selective commercial available medium Veal Infusion Broth (VIB) (Difco, 234420).

At the filing date of the present application the product catalogue ("Difco™/BBL™ Manual") from the provider BD Diagnostic Systems (www.bd.com) read in relation to the Veal Infusion Broth:

"Infusion from lean veal and peptone provide the nitrogen, vitamins, carbon and amino acids in veal infusion media. Sodium chloride maintains the osmotic balance of the formulations"; and The medium was prepared according to manufacture instructions by suspending 25 g of the Veal Infusion Broth powder in 1 L of purified water (2.5% solution) and heat with frequent agitation and boil for 1 minute to completely dissolve the powder.

A 2.5% Veal Infusion Broth solution comprised per liter:

| Lean Veal, Infusion: | 10 g |
| Proteose Peptone: | 10 g |
| Sodium Chloride | 5 g |

The medium was distributed into sterile bottles and autoclaved for 15 min at 121° C.

Bile Salt Solutions/Medium:

Mixtures of bile salts were prepared mimicking the physiological composition and concentration of bile salts in pig bile and the bile salts were dissolved in the Veal Infusion Broth medium as prepared above to give a final bile salt concentration of 8 mM.

The conjugated bile salts were taurodeoxycholate (Sigma T-0875, U.S.) and glycodeoxycholate (Sigma G-9910, U.S.) and the deconjugated bile salt deoxycholate (Sigma D-5670 U.S.) and the final 8 mM mixed bile salt solution contained 60% of the taurodeoxycholate, 30% of the glycodeoxycholate and 10% of deoxycholate. Before autoclaving for 15 minutes at 121° C., the solutions were adjusted to pH 7.4 using sodium hydroxide. The prepared 8 mM bile salt medium, were diluted to get bile salt concentrations of 0, 1, 2, 4, 6 and 8 mM.

The bile salts were added to the Veal Infusion Broth medium in a concentrated form.

Accordingly, the final amount of lean veal infusion, Proteose Peptone and Sodium chloride were essentially as for the 2.5% Veal Infusion Broth medium before the bile salts were added.

Spore Suspensions

To distinguish between vegetative cells and spores and to ensure pure spore products for inoculation, the spore counts of the bacillus product were determined using +/−heat treatment at 80° C. for 10 min. After heat treatment and subsequent cooling to room temperature, serial 10-fold dilutions were conducted in saline peptone water. Duplicates of Tryptose Blood Agar plates (Difco 0232-01) were inoculated with 0.1 ml from the appropriate decimal dilutions. The plates were incubated at 37° C. until the next day. Based on preceding spore count determinations of the products, spore suspensions were prepared in sterile distilled water to reach final calculated spore concentration of $10^8$ CFU/ml. The counts of vegetative cells and spores in the final inocula were determined using the method described above. The final concentration of $10^8$ CFU/ml corresponded to a start $OD_{630}$ at 0.2-0.3.

Growth Measurement: Optical Density Measurements

Sterile flat bottom 96 well microtiter plates were used (Greiner Bio-one GmbH, Germany). Each well was filled with 0.150 ml VIB inoculated with spores (~$1 \times 10^8$ spores per ml equivalent/corresponding to a start $OD_{630}$~0.2-0.3) and the plates were incubated for 20 hours at 37° C. with a 1 minute shaking cycle of intensity 4 (high) before each reading.

To avoid condensation on the inside of the plate cover, the lids were exposed to a dilute solution of Triton X-100.

The germination and outgrowth kinetics of Bacillus strains were measured using a spectrophotometer at wavelength 630 nm ($OD_{630}$) (Bio-tek Instruments, Inc. VE). Readings were performed with 10 minute intervals and analyzed using the KC4™ software (Bio-tek Instruments, Inc., USA). After 20 h, data were exported to Excel® spreadsheets for further analysis, imported in SAS version 9.0 and statistically analyzed.

Example 2

Amino Acid Assay

The method to measure and quantify the amino acids produced by the bacillus cells used in this study is a standard GC-MS method for aqueous samples, using methyl chloroformate as derivatization agent.

Growth of Bacillus Cells

The Bacillus cells are inoculated and grown in a minimal salts growth medium at 37° C., 150 rpm and grown for 2 days and amount of amino acid is then measured in the supernatant as described below.

The bacillus cells are propagated in a Minimal Salts Medium according to Chapman (1972) with the following composition:

| | |
|---|---|
| $(NH_4)_2SO_4$ (Merck 1.01217.1000) | 1 g/l |
| $K_2HPO_4$ (Merck 1.05101.1000) | 7 g/l |
| $KH_2PO_4$ (Merck 1.04873.1000) | 3 g/l |
| $MgSO_4 \cdot 7H_2O$ (Merck 1.05886.1000) | 0.1 g/l |

Autoclaved for 15 min at 121° C. and added autoclaved glucose to a final concentration of 0.5%.

Incubation is done in tubes with 10 ml medium for 2 days at 37° C. and 150 rpm.

Amino Acid Assay

The amino acid assay is carried out on cell supernatants, since the amino acids are secreted to the media. Samples are sterile filtered and kept at −20° C. until analysis.

Reagents:
Reagent 1: Internal standard solution. Norvaline 1 mM: 0.0172 g Norvaline+100 ml MQW
Reagent 2: Methanol/Pyridine 32/8 (v/v) (Catalysator)
Reagent 3: Methyl Chloroformate p.a. (MCF) (Derivatization agent)
Reagent 4: 1% $MCF/CHCl_3$ (v/v) (Extraction): 1 ml Methyl Chloroformate p.a.+Chloroform ad 1000 ml.

Sample Preparation:
Pipette 150 µl (25 µl+125µ MQW) sample into 2 ml injection vial.
Add 150 µl IS
Add 200 µl 1-Methanol/Pyridine 32/8% (v/v). Mix well.
Add 25 µl MCF (Methyl Chloroformate). Mix well until gas development occurs.
Add 500 µl 1% $MCF/CHCl_3$ (v/v), cap and mix vigorously. Phase separation occurs within minutes. If phase separation is too slow, centrifuge the vial (500 rpm/10 min).
If Norvaline is used as antimetabolite, an external standard or another suitable internal standard should be used instead, and the 150 µl IS substituted with either MQW or sample.

Samples are run on GC-MS with a standard amino acid column and protocol.

Example 3

Selection of Bile Resistant *Bacillus subtilis* Cell DSM 19467

The starting bacillus cell was the *Bacillus subtilis* cell GalliPro®.

GalliPro® was mutagenized to get a pool of new individual bacillus cells. Spores were made and selected for rapid germination and outgrowth from spore to vegetative cell in presence of a bile salt medium comprising 4 and 6 mM bile salt a described in example 1 above.

*Bacillus subtilis* cell DSM 19467 was selected. Table 1 below shows germination and outgrowth data.

Time (hours) from $10^8$ CFU/ml corresponding to OD 0.2-0.3 until OD 0.4 is reached (mean of 3 replicates).

| B. subtilis | 4 mM bile | 6 mM bile |
|---|---|---|
| Existing product GalliPro ® (DSM 17231) | >20 | >20 |
| Bile tolerant (DSM 19467) | 13 h 40 m | 15 h |
| Commercial product: Calsporin | >20 | >20 |

Some of the data of this example was made by testing phytase overexpressing DSM 19489. But for the technical result of this example this is herein relatively irrelevant since DSM 19467 has germination and outgrowth roughly as DSM 19489. See PCT/EP2008/057296 for further details.

Conclusion

DSM 19467 is a bile resistant strain and clearly germinating and outgrowing faster than GalliPro®.

Example 4

Selection of Amino Acid Over-Producing Bacillus Cells from DSM 19467

The starting bacillus cell was the *Bacillus subtilis* cell DSM 19467 selected in example 3.

DSM 19467, either wildtype or mutants produced by, e.g., UV-mutagenesis, was grown on Minimal Salts Medium agar, described in example 2B above and added 1.5% agar, containing amino acid analogues in suitable inhibitory amounts. Depending on the amino acid to be over-expressed various amino acid analogues could be used, e.g., norvaline or 4-aza-DL-leucine for overproducing leucine (Bardos, 1974, Topics in Current Chemistry 52, 63-98). Colonies resistant to the amino acid analogue were picked, grown in Minimal Salts Medium and assayed for amino acid production. The vegetative cells were selected for producing high amount of amino acid by using the GC-MS method described in example 2B above.

High amino acid producing *Bacillus subtilis* cell was selected.

Results of Amino Acid Measurements

A number of strains were selected which were producing the essential amino acid leucine in an amount that was significant higher than the reference bacillus cell DSM 19467.

A number of the selected strains produced at least 5 times more leucine than DSM 19467.

Conclusions:

This example shows that one can routinely—based on the instructions herein—screen and identify a strain, which produces at least one essential amino acid (here exemplified by leucine) in an amount that was significant higher than the reference bacillus cell DSM 19467.

DSM 19467 is originating from GalliPro® and is not selected for high essential amino acid production. Accordingly, it is believed that GalliPro® produces roughly the same amount of essential amino acid as DSM 19467.

Example 5

Bile Resistance "Check" of High Essential Amino Acid Producing Bacillus Cells Preferred high essential amino acid producing bacillus cells selected in example 4 are re-checked for their ability of rapid germination and outgrowth from spore to vegetative cells as described in example 1.

The results are that they—as expected—have maintained roughly the same good rapid germination and outgrowth as the starting cell DSM 19467 used to obtain them.

References
1. Antonie Van Leeuwenhoek. 2006 August; 90(2):139-46. Epub 2006 July 4
2. US2003/0124104A
3. U.S. Pat. No. 6,255,098
4. PCT/EP2008/057296

The invention claimed is:

1. A Bacillus composition comprising from $10^5$ to $10^{12}$ CFU/g *Bacillus subtilis* spore cells, wherein:
    (a) the *B. subtilis* strain is derived from DSM 19467;
    (b) the *B. subtilis* spores have a germination and outgrowth from spore to vegetative cell, in the presence of a bile salt medium comprising 4 mM bile salt or in the presence of a bile salt medium comprising 6 mM bile salt, such that the *B. subtilis* spores reach a vegetative cell growth point of 0.4 OD630 within less than 18 hours or 19 hours; and
    (c) the *B. subtilis* vegetative cells overproduce at least one desired compound in comparison to the mother strain, DSM 19467, when grown under identical conditions.

2. The Bacillus composition of claim 1, wherein the desired compound is an enzyme.

3. The Bacillus composition of claim 2, wherein the enzyme is phytase or mannanase.

4. The Bacillus composition of claim 1, wherein the desired compound is an amino acid.

5. The Bacillus composition of claim 4, wherein the amino acid is selected from the group consisting of phenylalanine, valine, threonine, tryptophan, isoleucine, methionine, leucine, lysine, cysteine, tyrosine, histamine, and arginine.

6. The Bacillus composition of claim 1, wherein the bacillus spore cells are present as dried spore cells.

7. A method for isolating a novel *Bacillus subtilis* cell which germinates and outgrows rapidly in the presence of a bile salt and which overproduces at least one desired compound, comprising:
    (a) subjecting vegetative cells grown from an isolated spore cell of *B. subtilis* strain DSM 19467 to mutagenesis, thereby obtaining a pool of individual vegetative cells which retain rapid germination and outgrowth in the presence of a bile salt;
    (b) selecting a vegetative cell from the pool of step (a), which has a germination and outgrowth from spore to vegetative cell in the presence of a bile salt medium comprising 4 mM bile salt or in the presence of a bile salt medium comprising 6 mM bile salt, such that the bacillus spores reach a vegetative cell growth point of 0.4 OD630 within less than 18 hours or 19 hours, and which overproduces said at least one desired compound in comparison to the mother strain, DSM 19467, when grown under identical conditions.

* * * * *